United States Patent
Steinman et al.

(10) Patent No.: US 7,070,780 B2
(45) Date of Patent: Jul. 4, 2006

(54) TREATMENT OF DEMYELINATING AUTOIMMUNE DISEASE WITH ORDERED PEPTIDES

(75) Inventors: Lawrence Steinman, Palo Alto, CA (US); Pedro Jose Ruiz, Redwood City, CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 280 days.

(21) Appl. No.: 10/152,654

(22) Filed: May 20, 2002

(65) Prior Publication Data

US 2002/0137681 A1 Sep. 26, 2002

Related U.S. Application Data

(62) Division of application No. 09/606,254, filed on Jun. 28, 2000, now Pat. No. 6,531,130.

(60) Provisional application No. 60/142,479, filed on Jul. 6, 1999.

(51) Int. Cl.
*A61K 39/00* (2006.01)
*A61K 38/04* (2006.01)
*A61K 38/08* (2006.01)
*A61K 38/17* (2006.01)

(52) U.S. Cl. .............................. 424/184.1; 424/185.1; 530/325; 530/326; 530/327; 530/328

(58) Field of Classification Search ............. 424/185.1, 424/325–328; 530/325–328, 184.1, 185.1
See application file for complete search history.

(56) References Cited

U.S. PATENT DOCUMENTS

| | | |
|---|---|---|
| 3,817,837 A | 6/1974 | Rubenstein et al. |
| 3,849,550 A | 11/1974 | Teitelbaum et al. |
| 3,850,752 A | 11/1974 | Schuurs et al. |
| 3,853,914 A | 12/1974 | Goldstein et al. |
| 3,905,654 A | 9/1975 | Tribe |
| 4,043,989 A | 8/1977 | Schneider et al. |
| 4,069,105 A | 1/1978 | Singh |
| 4,156,081 A | 5/1979 | Singh et al. |
| 6,531,130 B1 * | 3/2003 | Steinman et al. ........ 424/185.1 |

OTHER PUBLICATIONS

Stryer et al, in Biochemistry, Third edition, W H Freeman Company, New York, pp. 31-33, 1998.*
Van Noort et al, International Reivew of Cytology 178: 127-205, 1998.*
Ngo et al, 1994, The Protein Folding Problem and Tertiary Structure Prediction, pp. 492-495.*
Aharoni et al. (Sep. 1997), "Copolymer 1 Induces T Cells of the T Helper Type 2 that Crossreact with Myelin Basic Protein and Suppress Experimental Autoimmune Encephalomyelitis." *Proc. Natl. Acad. Sci. USA*, vol. 94:10821-10826.
Fridkis-Hareli et al. (1999), "Bonding Motifs of Copolymer 1 to Multiple Sclerosis and Rheumatoid Arthritis-Associated HLA-DR Molecules." *Journal of Immunology*, vol. 162:4697-4704.
Hafler et al. (1997), "Oral Administration of Myelin Induces Antigen-Specific TGF-β1 Secreting T Cells in Patients with Multiple Sclerosis," *Ann. NY Acad. Sci.*, vol. 835:120-131.
Karin et al. (Dec. 1994), "Reversal of Experimental Autoimmune Encephalomyelitis by a Soluble Peptide Variant of a Myelin Based Protein Epitope: T Cell Receptor Antagonism and Reduction of Interferon γ and Tumor Necrosis Factor α Production." *J. Exp. Med.*, vol. 180:2227-2237.
Kennedy et al. (1997), "Induction of Antigen-Specific Tolerance for the Treatment of Ongoing, Relapsing Autoimmune Encephalomyelitis." *Journal of Immunology*, vol. 159:1036-1044.
Marušić et al. (Aug. 18, 1997), "Tolerance Induction and Autoimmune Encephalomyelitis Amelioration After Administration of Myelin Basic Protein-Derived Peptide." *J. Exp. Med.*, vol. 186(4):507-515.
Merrifield, R.B. (Jul. 20, 1963), "Solid Phase Peptide Synthesis." *J. Am. Chem. Soc.*, vol. 85:2149-2154.
Miller et al. (1998), "Treatment of Multiple Sclerosis with Copolymer-1 (Copaxone ®): Implicating Mechanisms of Th1 to Th2/Th3 Immune-Deviation." *Journal of Neuroimmunology*, vol. 92:113-121.
Ngo et al., in The Protein Folding Problem and Tertiary Structure Prediction, 1994, pp. 491-495.

(Continued)

*Primary Examiner*—Christina Chan
*Assistant Examiner*—Phuong Huynh
(74) *Attorney, Agent, or Firm*—Townsend & Townsend & Crew

(57) ABSTRACT

Compositions and methods are provided for the treatment of demyelinating autoimmune disease. Therapeutic doses are administered of an ordered peptide comprising a repeated motif {SEQ ID NO: 1} $[^1E^2Y^3Y^4K]_n$, where n is from 2 to 6. Some specific peptides of interest include those having the sequence {SEQ ID NO:4} EYYKEYYKEYYK. The peptide may consist only of the ordered repeats, or may be extended at either termini by the addition of other amino acid residues. For therapy, the peptides may be administered topically or parenterally, e.g. by injection at a particular site, including subcutaneously, intraperitoneally, intravascularly, or the like or transdermally, as by electrotransport. In a preferred embodiment, subcutaneous injection is used to deliver the peptide. The subject methods are used for prophylactic or therapeutic purposes. The compositions of the invention may also contain other therapeutically active agents, e.g. immunosuppressants, β-interferon, steroids, etc.

6 Claims, 1 Drawing Sheet

OTHER PUBLICATIONS

Reiseter et al. (1998), "Treatment of Murine Experimental Autoimmune Encephalomyelitis with a Myelin Based Protein Peptide Analog Alters the Cellular Composition of Leukocytes Infiltrating the Cerebrospinal Fluid." *Journal of Neuroimmunology,* vol. 91:156-170.

Sakai et al. (Dec. 1989), "Prevention of Experimental Encephalomyelitis with Peptides that Block Interaction of T Cells with Major Histocompatibility Complex Proteins." *Proc. Natl. Acad. Sci. USA,* vol. 86:9470-9474.

Steinman et al. (1995), "Major T-Cell Responses in Multiple Sclerosis." *Mol. Med. Today,* vol. 1:79-83.

Steinman, Lawrence (Jun. 29, 1995), "Presenting an Odd Antigen." *Nature,* vol. 375:739-740.

Steinman, Lawrence (Jan. 13, 1977), "Regulation of Autosensitization to Encephalitogenic Myelin Basic Protein by Macrophage-Associated and Soluble Antigen." *Nature,* vol. 265:173-175.

Warren et al. (Nov. 1995), "Fine Specificity of the Antibody Response to Myelin Basic Protein in the Central Nervous System in Multiple Sclerosis: The Minimal B-Cell Epitope and a Model of its Features." *Proc. Natl. Acad. Sci. USA,* vol. 92:11061-11065.

Wraith et al. (Oct. 20, 1989), "Antigen Recognition in Autoimmune Encephalomyelitis and the Potential for Peptide-Mediated Immunotherapy." *Cell,* vol. 59:247-255.

* cited by examiner

TREATMENT OF DEMYELINATING AUTOIMMUNE DISEASE WITH ORDERED PEPTIDES

CONTINUITY

The present application is a divisional of U.S. patent application Ser. No. 09/606,254, filed on Jun. 28, 2000, which has now issued as U.S. Pat. No. 6,531,130, which claims priority to U.S. patent application Ser. No. 60/142,479, filed Jul. 6, 1999.

GOVERNMENT SUPPORT

The research was supported in least in part by a grant from the National Institutes of Health, grant no. ROI NS 18235. The Government may have certain rights in this invention.

BACKGROUND OF THE INVENTION

Introduction

Multiple sclerosis (MS) is an acquired, inflammatory, demyelinating disease of the central nervous system (CNS). In MS, cells of the immune system invade and destroy myelin, the fatty material that insulates nerves in the brain and spinal cord; other CNS cells produce a hardened sclerotic lesion (plaque) around the multiple demyelinated sites. Neurologic findings suggest lesions in separate areas of the CNS that have occurred at different times.

Multiple sclerosis (MS) is the most common autoimmune disease involving the nervous system. In the United States approximately 250,000 individuals suffer from MS. The cause of the disease is unknown, but genetic factors are important. The concordance rate among monozygotic twins is 30%, a 10-fold increase over dizygotic twins or first-degree relatives. The higher incidence rate among monozygotic twins emphasizes the importance of genetic factors, but the discordance rate of 70% among identical twins illuminates the role of nongenetic factors on disease penetrance. Among genetic factors, HLA class II genes exert an influence, with HLA DR2 carrying a 4-fold relative risk for northern European caucasoids.

A typical presentation of MS involves an initial course, running for several years to more than a decade, manifest by episodes of relapse followed by remission. Relapses often follow an episode of a viral infection of the upper respiratory system or gastrointestinal tract. In about one half of MS cases the disease progresses to a more chronic phase. Clinical problems may include disturbances in visual acuity, sometimes culminating in blindness; double vision; motor disturbances affecting walking and use of the hands; incoordination; bowel and bladder incontinence; spasticity; and sensory disturbances including loss of touch, pain, and temperature and proprioception. The pathology of the disease lies entirely in the central nervous system and is characterized by a classic picture of inflammation surrounding venules and extending into the myelin sheath.

Immune responses to various components of the myelin sheath have been detected in MS patients, including myelin basic protein (MBP), proteolipid (PLP), transaldolase, and 2',3' cyclic nucleotide 3'phosphodiesterases (CNP), as well as two members of the immunoglobulin supergene family found in the myelin sheath, myelin oligodendroglial glycoprotein (MOG) and myelin-associated glycoprotein (MAG) (Steinman et al. (1995) *Mol. Med. Today* 1:79–83). In addition, some inducible heat shock proteins, including crystallin-B, can be detected in glial cells in MS lesions and can stimulate an immune response in MS patients.

A key immune response is targeted to certain regions of myelin basic protein. The major T and B cell response in the central nervous system of MS patients who are HLA DR2 (about two thirds of patients) is directed to a region between residues 84 and 103 of MBP (Steinman (1995) Nature 375:739–740; Warren et al. (1995) *P.N.A.S.* 92:11061–11065). The B cell response to MBP in MS has also been studied extensively. IgG purified from brain lesions reacted with the same region of MBP, p85–96, that is the immunodominant T cell epitope in MS patients who are HLA DR2b (DRB1*1501) and overlaps with the T cell epitope in MS patients who are DR2a (DRB5*0101).

Relevant Literature

Copolymer-1 is a mixture of polypeptides composed of alanine, glutamic acid, lysine, and tyrosine in a molar ratio of approximately 6:2:5:1, respectively. It is synthesized by chemically polymerizing the four amino acids forming products with average molecular weights of 23,000 daltons (U.S. Pat. No. 3,849,550). Cop 1 binds promiscuously, with high affinity and in a peptide-specific manner to purified MS-associated HLA-DR2 (DRB1*1501) and rheumatoid arthritis-associated HLA-DR1 (DRB1*0101) or HLA-DR4 (DRB1*0401) molecules (Fridkis-Hareli et al. (1999) *J Immunol* 162(8):4697–704). Protruding N-terminal ends of Cop 1 bound to HLA-DR1, -DR2, or -DR4 molecules were then treated with aminopeptidase I, followed by elution, HPLC, and pool sequencing. In contrast to untreated or unbound Cop 1, this material exhibited distinct motifs at some positions with increases in levels of E at the first and second cycles, of K at the second and third cycles, and of Y (presumably at P1 of the bound peptide) at the third to fifth cycles, regardless of the HLA-DR molecule employed. No preference was seen at the following cycles that were mainly A.

Cop-1 has been recently approved as a treatment for relapsing multiple sclerosis (MS). Evidence demonstrates that Cop-1 induces active suppression of CNS-inflammatory disease in animal models (Aharoni et al. (1997) *P.N.A.S.* 94(20):10821–6). In humans, Copaxone treatment was found to lead to a significant reduction in the mean annual relapse rate and stabilization of disability. The treatment was accompanied by an elevation of serum IL-10 levels, suppression of the pro-inflammatory cytokine TNF alpha mRNA, and an elevation of the anti-inflammatory cytokines TGF-beta and IL4 mRNAs in PBLs (Miller et al. (1998) *J Neuroimmunol* 92(1–2):113–21).

Treatment of murine experimental autoimmune encephalomyelitis with a myelin basic protein peptide analog is described by Reiseter et al. (1998) *J Neuroimmunol* 91(1–2): 156–70. A single administration of the MBP peptide analog, Ac1–11[4Y], reduced disease severity, accompanied by a dramatic and selective loss of neutrophil pleiocytosis. A longer course of peptide therapy resulted in complete recovery from clinical signs of disease, and decreased pleiocytosis by all cell types. Wraith et al. (1989) *Cell* 59:247–255 describe antigen recognition in autoimmune encephalomyelitis and the potential for peptide mediated immunotherapy. Sakai et al. (1989) *Proceedings of the National Academy of Sciences USA* 86:9470–9474 describe the prevention of experimental encephalomyelitis with peptides that block interaction of T cells with major histocompatibility complex proteins. Karin et al. (1994) *J.E.M.* 180:2227–2237 demonstrate the reversal of experimental autoimmune encephalomyelitis by a soluble variant of a myelin basic protein epitope.

It has been reported that administration of myelin basic protein can lead to immune tolerance (see, for example, Steinman et al. (1977) Nature 265:173; Tonegawa (1997) J Exp Med 186(4):507–15;Hafler et a. (1997) Ann N Y Acad Sci 835:120–31; Kennedy et al. (1997) J Immunol 159(2): 1036–44). Various forms of Ag-specific tolerance have been demonstrated, included the administration of peptide coupled splenocytes, i.p. administration in incomplete adjuvant, oral and nasal administration.

SUMMARY OF THE INVENTION

Methods and compositions are provided for the treatment of demyelinating autoimmune diseases, including experimental autoimmune encephalomyelitis and multiple sclerosis, by administering to the host a peptide comprising the ordered amino acid motif {SEQ ID NO:1} $[^1E^2Y^3Y^4K]_n$, where n is from 2 to 6. The ordered motif may start at residue 1, as shown, or may start at a different position, e.g. {SEQ ID NO:2} YYKEYYKE; {SEQ ID NO:3} YKEYYKEY; etc.

The compositions of the present invention may be synthesized by conventional methods known in the art, e.g. expression in a recombinant system, solid phase peptide synthesis, etc. The peptide is formulated in a biologically acceptable carrier, and administered by a route to enhance the autoimmune suppressive effects of the treatment. Typically, the peptides are administered to patients suffering from multiple sclerosis on a regular basis. In a preferred embodiment, the composition is lyophilized and formed into an aqueous solution suitable for sub-cutaneous injection.

DETAILED DESCRIPTION OF THE EMBODIMENTS

Figure 1:
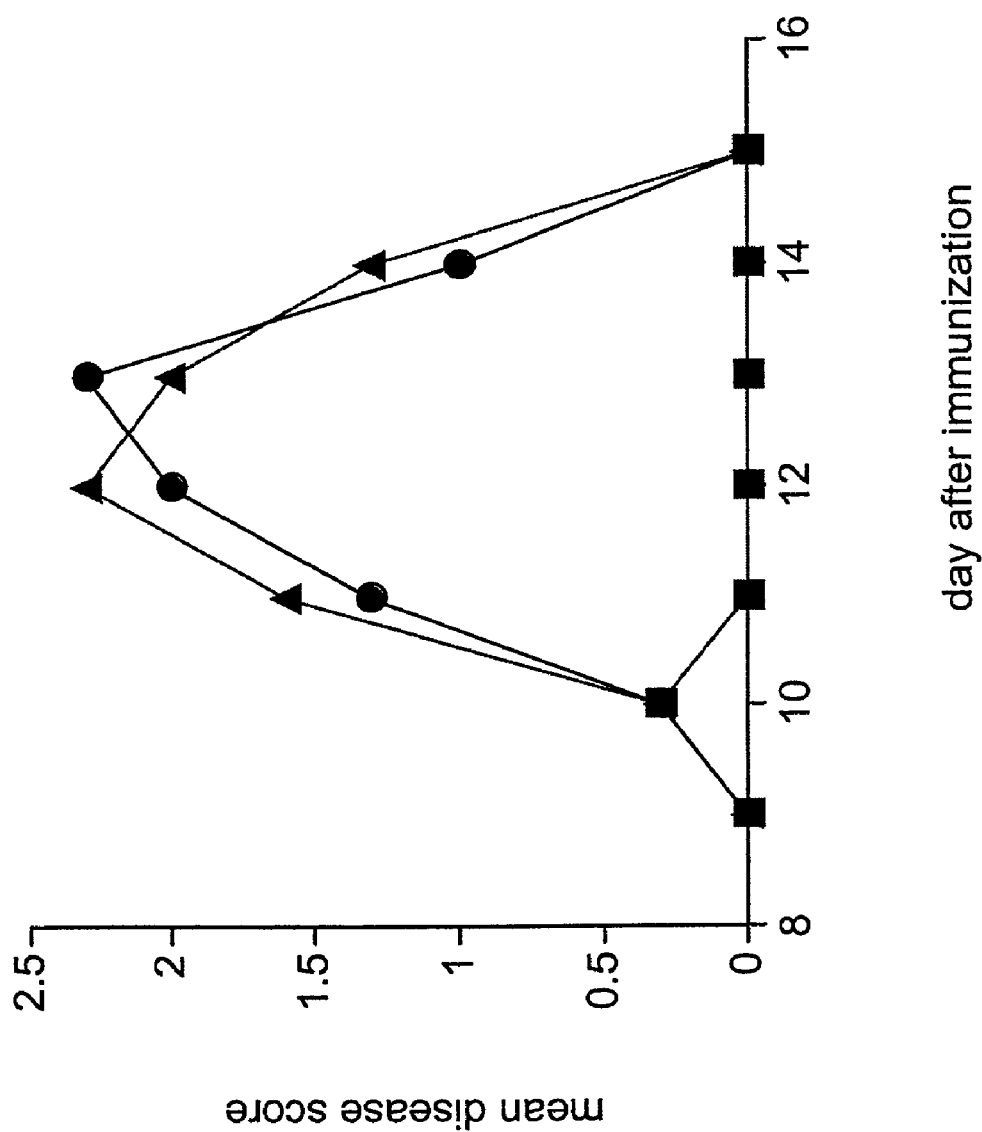
FIG. 1 is a graph depicting the prevention of EAE in rats treated with ordered peptides. Figure legend: Ordered peptide {SEQ ID NO:4} EYYKEYYKEYYK prevents the development of EAE in Lewis rats. Animals were injected with an emulsion of 0.1 mg of MBPp85–99 in complete Freund's adjuvant for EAE induction. Ten days later, when the clinical manifestations of disease became apparent, a single intra-peritoneal dose of peptide {SEQ ID NO:4} EYYKEYYKEYYK (squares), {SEQ ID NO:5} KYYKYYKYYKYY (triangles), or PBS (circles)was administered. Results are expressed as mean disease score of groups of six animals.

Demyelinating autoimmune diseases, including experimental autoimmune encephalomyelitis and multiple sclerosis, are treated by administering a therapeutic ordered peptide. The ordered peptides are formulated in a pharmaceutically acceptable carrier for a convenient route of administration, which may be subcutaneous, oral, by inhalation, etc. as known in the art.

The subject methods are used for prophylactic or therapeutic purposes. As used herein, the term "treating" is used to refer to both prevention of disease, and treatment of pre-existing conditions. The prevention of autoimmune disease is accomplished by administration of the peptide prior to development of overt disease. The treatment of ongoing disease, in order to stabilize or improve the clinical symptoms of the patient, is of particular interest. Such treatment is desirably performed prior to loss of function in the affected tissues. Evidence of therapeutic effect may be any diminution in the severity of disease, particularly measuring the frequency of relapses in patients being treated with the ordered peptides, which may be the length of time the patient is relapse free, or the mean relapse frequency.

Therapeutic ordered peptides of the present invention comprise the ordered amino acid motif {SEQ ID NO:1} $[^1E^2Y^3Y^4K]_n$, where n is from 2 to 6. The ordere motif may start at residue 1, as shown, or may start at a different position, e.g. {SEQ ID NO:6} YYKEYYKEYYKE; {SEQ ID NO: 7} KEYYKEYYKEYY, etc. The total length of the ordered peptide sequence will usually be at least about 8 amino acids in length and not more than about 24 amino acids in length, usually at least about 10 and not more than about 20. Specific peptides of interest include the sequence {SEQ ID NO:4} EYYKEYYKEYYK. The peptide may consist only of the ordered repeats, or may be extended at either termini by the addition of other amino acid residues.

Modification and changes may be made in the structure of the ordered peptide and still obtain a molecule having the desired characteristic of suppressing demyelinating autoimmune disease. The desired properties may be determined, at least in part, in an in vitro assay, where binding to the MHC antigen HLA-DR, particularly HLA-DR2 (DRB1*1501), is indicative of the relevant biological activity.

For example, certain amino acids may be substituted for other amino acids in a protein structure without appreciable loss of function. It will be understood by one of skill in the art that various changes (such as to protein stability or efficiency) may be made in the sequence of the ordered peptide without appreciable loss of their biological utility or activity, particularly as to the additional of terminal amino acids. So long as a change maintains the binding properties and immunological activity, the resultant protein will be considered a biologically functional equivalent for the purposes of the invention.

The peptides may be provided in a variety of ways, being joined to non-wild-type flanking regions, as fused proteins, joined by linking groups or directly covalently linked through cysteine (disulfide) or peptide linkages. The peptides may be joined to a single amino acid at the N- or C-terminus or a chain of amino acids. The fused peptides may be extended to provide convenient linking sites, e.g. cysteine or lysine, to enhance stability, to bind to particular receptors, to provide for site-directed action, to provide for ease of purification, to alter the physical characteristics (e.g. solubility, charge, etc.), to stabilize the conformation, etc. The peptide may be N-terminal, C-terminal or internal in relation to these added sequences.

The peptide may be linked through a variety of bifunctional agents, such as maleimidobenzoic acid, methyldithioacetic acid, mercaptobenzoic acid, S-pyridyl dithiopropionate, etc. The oligopeptides may be linked to proteins to provide site-directed action. The oligopeptides may be linked, particularly by an intracellular cleavable linkage, to antibodies for site directed action. For conjugation techniques, see, for example, U.S. Pat. Nos. 3,817,837; 3,853, 914; 3,850,752; 3,905,654; 4,156,081; 4,069,105; and 4,043,989, which are incorporated herein by reference. The oligopeptides may also be modified by incorporation into the lumen of vesicles, e.g. liposomes, which in turn may be bound to ligands or receptors for direction to particular cells or tissue.

For therapy, the peptides may be administered topically or parenterally, e.g. by injection at a particular site, including subcutaneously, intraperitoneally, intravascularly, or the like or transdermally, as by electrotransport. In a preferred embodiment, subcutaneous injection is used to deliver the peptide. The oligopeptides may also be administered in a sustained release formulation or osmotic pump, to provide a depot of active peptide for slow release over an extended period. Such delivery may decrease the dosage of drug required and may also decrease the number of treatments necessary to achieve a therapeutic effect.

The oligopeptides of this invention may be prepared in accordance with conventional techniques, such as synthesis, recombinant techniques, or the like. For example, solid-phase peptide synthesis involves the successive addition of amino acids to create a linear peptide chain (see Merrifield (1963) *J. Am. Chem. Soc.* 85:2149–2154). Production of the peptide by recombinant DNA technology may also be performed. One first synthesizes or otherwise creates a nucleic acid sequence that encodes the desired peptide. This coding sequence is operably connected to suitable control elements for expression, e.g. promoters, terminators, ATG start codon, and the like as known in the art. This expression construct is introduced into a suitable host cell, and the recombinant protein that is produced is isolated. Alternatively, the coding sequence is introduced into the host to be treated for long term therapy, for example by inserting an expression construct into muscle or long-lived hematopoietic cells for therapy. The expression vector may be a plasmid, viral vector, including retrovirus, adenovirus, etc., and may be introduced by transduction, DNA vaccination, etc.

Pharmaceutically acceptable salts of the peptides also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

The subject methods are used to treat individuals suffering from demyelinating autoimmune disease. Diagnosis of suitable patients may utilize a variety of criteria known to those of skill in the art. A quantitative increase in myelin autoreactive T cells with the capacity to secrete IFN-gamma is associated with the pathogenesis of MS and EAE. During the presymptomatic period there is infiltration of leukocytes into the cerebrospinal fluid, inflammation and demyelination. Family histories and the presence of the HLA haplotype DRB1*1501,DQA1*0102, DQB1*0602 are indicative of a susceptibility to the disease. Treatment during the early stages of the disease is preferred, in order to slow down or arrest the further loss of neural function.

Patients are diagnosed as having multiple sclerosis according to conventional clinical criteria. Such criteria rely on the presence of two attacks at least one month apart, where an attack is a sudden appearance of or worsening of an MS symptom or symptoms which lasts at least 24 hours; and more than one area of damage to central nervous system myelin. The damage to myelin must have occurred at more than one point in time and not have been caused by any other disease that can cause demyelination or similar neurologic symptoms.

MRI (magnetic resonance imaging) is the preferred method of imaging the brain to detect the presence of plaques or scarring caused by MS, although CT scans may also be used. Other symptoms include disability in mental, emotional, and language functions, movement and coordination, vision, balance, and the functions of the five senses. Evoked potential tests are electrical diagnostic studies which can show if there is a slowing of messages in the various parts of the brain, and may provide evidence of scarring along nerve pathways that is not apparent on a neurologic exam. Cerebrospinal fluid, usually taken by a spinal tap, may be tested for levels of cytokines, and for the presence of oligoclonal antibody band.

The therapeutic effect may be measured in terms of clinical outcome, or may rely on immunological or biochemical tests. Suppression of the deleterious T-cell activity can be measured by enumeration of myelin-reactive Th1 cells in spinal fluid, by quantitating the release of cytokines at the sites of lesions, or using other assays for the presence of autoimmune T cells known in the art. Alternatively, one may look for a reduction in symptoms of a disease, such as the damage to neural tissue observed in MS, or the decrease in the number or severity of attacks of MS suffered by MS patients. Damage to neural tissue can be assessed for example by magnetic resonance imaging (MRI) and measurement of the number and severity of lesions visible therein. Reduction in MS attack number or severity can be assessed for example by clinical evaluation of patients. Methods for both MRI and clinical evaluation are well-known in the art.

Various methods for administration may be employed. The formulation may be given orally, by inhalation, or may be injected, e.g. intravascular, intratumor, subcutaneous, intraperitoneal, intramuscular, etc. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc. to maintain an effective dosage level. In many cases, oral administration will require a higher dose than if administered intravenously.

The peptides of the invention can be incorporated into a variety of formulations for therapeutic administration. More particularly, the complexes can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the peptides can be achieved in various ways, including oral, buccal, rectal, parenteral, intraperitoneal, intradermal, transdermal, intracheal, etc., administration. The peptides may be systemic after administration or may be localized by the use of an implant that acts to retain the active dose at the site of implantation.

In pharmaceutical dosage forms, the peptides may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the peptides can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The peptides can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The peptides can be utilized in aerosol formulation to be administered via inhalation. The compounds of the present invention can be formulated into pressurized acceptable propellants such as dichlorodifluoromethane, propane, nitrogen and the like.

Furthermore, the peptides can be made into suppositories by mixing with a variety of bases such as emulsifying bases or water-soluble bases. The peptides of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing peptides is placed in proximity to the site of action, so that the local concentration of active agent is increased relative to the rest of the body.

The term "unit dosage form," as used herein, refers to physically discrete units suitable as unitary dosages for human and animal subjects, each unit containing a predetermined quantity of peptides of the present invention calculated in an amount sufficient to produce the desired effect in association with a pharmaceutically acceptable diluent, carrier or vehicle. The specifications for the novel unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The compositions of the invention may also contain other therapeutically active agents, e.g. immunosuppressants, β-interferon, steroids, etc. Of particular interest are combinations with other agents capable of additive or synergistic effect in achieving a therapeutic result, e.g. where a different or complementary pathway is affected by each of the active agents. Immunosuppressants of interest include cyclosporins A and G, FK-506, mycophenylate mofetil, rapamycin, azathioprine, antibodies for plasma membrane proteins associated with graft rejection, such as immunosuppressive oligopep/tides derived from MHC molecules. Antibacterial, antiviral and antifungal drugs may also be co-formulated in order to minimize the effects of immunosuppression.

Depending on the patient and condition being treated and on the administration route, the peptides will generally be administered in dosages of 0.01 mg to 500 mg V/kg body weight per day, e.g. about 20 mg/day for an average person. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. A typical dosage may be one injection daily.

Those of skill will readily appreciate that dose levels can vary as a function of the specific compound, the severity of the symptoms and the susceptibility of the subject to side effects. Some of the specific peptides are more potent than others. Preferred dosages for a given complex are readily determinable by those of skill in the art by a variety of means. A preferred means is to measure the physiological potency of a given compound.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the methods and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, and pressure is at or near atmospheric.

EXPERIMENTAL

Example 1

Ordered Peptides for immunomodulation Based on MHC-TCR Binding Motifs

The region between the amino acids 85 to 99 of myelin basic protein (MBP) contain the immunodominant epitope for T cells and autoantibodies in MS brain lesions. The main region of MBP recognized by T cells and autoantibodies, found in MS brain, is the core motif, {SEQ ID NO:8} HFFK, from MBPp87–99 in patients who are HLA DRB1*1501 DQB1*0602 (HLA DR2).

Previously, we have compared the structural requirements for autoantibody recognition to those of T cell clones reactive to MBP p87–99. Anti-MBP antibodies were affinity-purified from CNS lesions of 12 post-mortem cases studied. The MBP p87–99 peptide was immunodominant in all cases and it inhibited autoantibody binding to MBP by more than 95%. Residues contributing to autoantibody binding were located in a 10-amino acid segment p86–95 ({SEQ ID NO:9} VVHFFKNIVT) that also contained the MHC-T cell receptor contact residues for T cells recognizing MBP in the context of DRB1*1501 and DQB1*0602. In the epitope center, the same residues, {SEQ ID NO:10} VHFFK, were important for T cell binding and MHC recognition. Recently, the crystal structure of HLA-DR2 with MBPp85–99 was solved, confirming the prediction that K91 is the major TCR contact residue, while F90 is a major anchor into the hydrophobic P4 pocket of the MHC molecule.

Peptides were synthesized that contained repetitive sequences of three amino acids ordered to bind the pockets existing in MS related MHC molecules and therefore to interfere with the activation of pathogenic T cells. One of those predicted sequences ({SEQ ID NO:4} EYYKEYYKEYYK), was effective in preventing and treating experimental autoimmune encephalomyelitis in Lewis rats, an animal model of Multiple Sclerosis.

Materials and Methods

Animals. Female Lewis rats (6–8 weeks old), were purchased from Harlan Sprague Dawley (Indianapolis, Ind.)

Peptides. For immunization and disease reversal, peptides were synthesized on a peptide synthesizer (model 9050: MilliGen, Burlington, Mass.) by standard 9-fluorenylmethoxycarbonyl chemistry. Peptides were purified by HPLC. Structure was confirmed by amino acid analysis and mass spectroscopy. Peptides used for the experiments were: {SEQ ID NO:11} ENPVVHFFKNIVTPR (MBPp85–99), {SEQ ID NO:4} EYYKEYYKEYYK, {SEQ ID NO:5} KYYKYYKYYKYY.

EAE Induction. Synthetic peptide MBPp85–99 was dissolved in PBS to a concentration of 2 mg/ml and emulsified with and equal volume of Incomplete Freund's Adjuvant (IFA), supplemented with 4 mg/ml heat-killed *Mycobacterium tuberculosis* H37Ra (Difco Laboratories, Detroit, Mich.). Rats were injected subcutaneously with 0.1 ml of the peptide emulsion. Experimental animals were scored as follows: 0, no clinical disease; 1, tail weakness or paralysis; 2, hind limb weakness; 3, hind limb paralysis; 4, forelimb weakness or paralysis; 5, moribund or dead animal.

EAE Treatment. Rats previously immunized with MBPp85–99 for EAE induction were scored from day eight after peptide injection. On the day of mean disease onset, animals were injected intraperitoneally with a solution of 0.5 mg of peptide in PBS (one dose of 0.25 ml).

RESULTS

Injection of ordered peptides containing TCR-MHC binding motifs reverse the development of EAE. In order to test the potential of the predicted sequences to revert the development of ongoing EAE we delivered a single dose of a PBS solution containing 0.5 mg of peptide in 0.25 ml. As seen in the graph, this dose is enough to treat the ongoing disease, when compared with the control groups.

What is claimed is:

1. A method of treating multiple sclerosis, the method comprising:
   administering to a patient suffering from multiple sclerosis a pharmaceutical formulation comprising an effective dose of a peptide consisting of the ordered amino acid motif set forth in SEQ ID NO: 1, (EYYK)$_n$, wherein n is from 2 to 6; and a pharmaceutically acceptable carrier;
   wherein the clinical symptoms of multiple sclerosis are reduced.

2. The method of claim 1, wherein n=3.

3. The method of claim 1, wherein said peptide consists of the amino acid sequence EYYKEYYKEYYK (SEQ ID NO:4).

4. The method of claim 1, wherein said administering comprises subcutaneous injection.

5. The method of claim 1, wherein said administering is performed daily.

6. The method of claim 1, wherein said patient suffering from multiple sclerosis has the HLA-DR2 (DRB1*1501) allele.

* * * * *

SEQUENCE LISTING

```
<160> NUMBER OF SEQ ID NOS: 11

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Glu Tyr Tyr Lys
 1

<210> SEQ ID NO 2
<211> LENGTH: 8
<212> TYPE: PRT
<213> ORGANISM: Artificial Sequence
```

```
<220> FEATURE:
<223> OTHER INFORMATION: Synthetic Peptide

<400> SEQUENCE: 2

Tyr Tyr Lys Glu Tyr Tyr Lys Glu
 1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 3

Tyr Lys Glu Tyr Tyr Lys Glu Tyr
 1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 4

Glu Tyr Tyr Lys Glu Tyr Tyr Lys Glu Tyr Tyr Lys
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

Lys Tyr Tyr Lys Tyr Tyr Lys Tyr Tyr Lys Tyr Tyr
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 6

Tyr Tyr Lys Glu Tyr Tyr Lys Glu Tyr Tyr Lys Glu
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 7

Lys Glu Tyr Tyr Lys Glu Tyr Tyr Lys Glu Tyr Tyr
 1               5                  10

<210> SEQ ID NO 8
<211> LENGTH: 4
<212> TYPE: PRT
<213> ORGANISM: Artificial Sequence
<220> FEATURE:
```

```
-continued

<223> OTHER INFORMATION: Synthetic Peptide

<400> SEQUENCE: 8

His Phe Phe Lys
 1

<210> SEQ ID NO 9
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 9

Val Val His Phe Phe Lys Asn Ile Val Thr
 1               5                  10

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 10

Val His Phe Phe Lys
 1               5

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 11

Glu Asn Pro Val Val His Phe Phe Lys Asn Ile Val Thr Pro Arg
 1               5                  10                  15
```